US00PP23795P2

(12) United States Plant Patent
Kordes

(10) Patent No.: US PP23,795 P2
(45) Date of Patent: Aug. 6, 2013

(54) MINATURE ROSE PLANT NAMED 'KORPOT003'

(50) Latin Name: *Rosa hybrida*
Varietal Denomination: KORpot003

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 44 days.

(21) Appl. No.: 13/385,358

(22) Filed: Feb. 14, 2012

(51) Int. Cl.
*A01H 5/00* (2006.01)

(52) U.S. Cl.
USPC ..... Plt./122

(58) Field of Classification Search
USPC ..... Plt./122
See application file for complete search history.

(56) References Cited

U.S. PATENT DOCUMENTS

PP19,358 P2 * 10/2008 Trees ..... Plt./227

OTHER PUBLICATIONS

Anonymous. "Kordana Potroses Special Miniature Roses" see p. 2. Available at http://www.kordes-rosen.com accessed May 20, 2013.*

* cited by examiner

*Primary Examiner* — Wendy C Haas

(57) ABSTRACT

A new and distinct variety of rose with long lasting, novel dark red flowers, and attractive foliage with very good disease resistance. It exhibits moderate growth and vigor, and it produces abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination:

The denomination of the new variety is 'KORpot003'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2006. The crossing was between an 'un-named seedling', the seed parent, and another 'un-named seedling' (both unpatented), the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot003'.

SUMMARY OF THE INVENTION

The new rose plant may be distinguished from its seed parent, an 'un-named seedling', by the following combination of characteristics:

1. The petal count of 'KORpot003' is double, whereas the petal count of its seed parent is semi-double.

2. The seed parent has medium red flowers, whereas 'KORpot003' has dark red flowers.

The new rose plant may be distinguished from its pollen parent, an 'un-named seedling' by the following combination of characteristics:

1. 'KORpot003' has medium peduncle length with medium blooms whereas the pollen parent has a long peduncle with small blooms.
2. 'KORpot003' has very good disease resistance, whereas the pollen parent has average disease resistance.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot003' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot003' was selected in May, 2007 from the seedling beds to be asexually propagated for further evaluation. The first asexual propagation of 'KORpot003' was done in May, 2007 at the inventor's nursery in Offenseth-Sparrieshoop, Germany by taking cuttings and subsequently rooting them.

This initial and other subsequent propagations conducted in controlled environments demonstrate that 'KORpot003' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot003'.

DETAILED BOTANICAL DESCRIPTION

The following is a description of 'KORpot003', as observed growing in October, 2011 in a nursery in Jackson County, Oreg. on plants 8 months of age. Color references are made using The Royal Horticultural Society (London, England) Colour Chart, 2001 except where common terms of color are used.

For a comparison, several physical characteristics of the rose variety 'KORpolare', a rose variety from the same inventor described and illustrated in U.S. Plant Pat. No. 18,840 and issued on May 27, 2008 are compared to 'KORpot003' in Chart 1.

CHART 1

| Characteristic | 'KORpot003' | 'KORpolare' |
|---|---|---|
| Petal count | 55-65 | 55 |
| Average number of petaloids | 3-6 | 8-12 |
| Average terminal leaflet size | 50 mm (l) × 30 mm (w) | 40 mm (l) × 22 mm (w) |

Parents:
- *Seed parent.*—'Un-named seedling'.
- *Pollen parent.*—'Un-named seedling'.

Classification:
- *Botanical classification.*—*Rosa hybrida* 'KORpot003'.
- *Commercial classification.*—Miniature rose.

FLOWER AND FLOWER BUD

Blooming habit: Recurrent.

Flower bud:
- *Size.*—Upon opening, 30 mm in length from base of receptacle to distal end of bud and 9 mm diameter at its widest point.
- *Bud form.*—Short. Pointed ovoid.
- *Bud color.*—As sepals first unfold, bud color is Red Group 53A. When ¼ open, the upper surface of petals is Red Group 53A, and the lower surface is Red Group 53A.
- *Sepals.*—Color: Upper surface Yellow-Green Group 146C. Lower surface Yellow-Green Group 146B. Size: Average 30-50 mm (l)×6-8 mm (w). Shape: Strong foliaceous appendages on 3 of the five sepals. Apex: cirrose. Base: Flat at union with receptacle. Quantity: Five. Surface texture: Upper side: Pubescent. Lower surface: Pubescent with a few stipitate glands. Margins: With stipitate glands and fine hairs.

Receptacle:
- *Surface.*—Smooth.
- *Color.*—Yellow-Green Group 146C.
- *Shape.*—Funnel.
- *Size.*—7 mm (h)×5 mm (w).

Peduncle:
- *Surface.*—With stipitate glands.
- *Length.*—30 to 50 mm average length.
- *Diameter.*—2 to 2.5 mm average diameter.
- *Color.*—Yellow-Green Group 146C.
- *Strength.*—Average.
- *Borne.*—Singularly.

Flower bloom:
- *Fragrance.*—None.
- *Duration.*—On the plant 14 to 16 days. Long lasting. As a cut flower, 6 to 8 days. Senesced petals drop away cleanly from plant.
- *Size.*—Small for a miniature rose. When open, the average flower diameter is 50 mm and the average flower height is 20 mm.
- *Form.*—Shape of flower when viewed from the side: Upon opening, upper part: Flattened convex. Upon opening, lower part: Flattened convex. Open flower, upper part: Flat. Open flower, lower part: Concave.

Color:
- *Upon opening, petals.*—Outermost petals: Outer Side: Red Group 53A. Inner Side: Red Group 53A. Innermost petals: Outer Side: Red Group 53A. Inner Side: Red Group 53A.
- *Upon opening, basal petal spots.*—Basal petal spot, outermost petals: Outer Side: White Group N155D. Inner Side: White Group N155C. Basal petal spot, innermost petals: Outer Side: White Group 155 C. Inner Side: White Group N155B.
- *After opening, petals.*—Outermost petals: Outer Side: Red Group 53B. Inner Side: Red Group 53A. Innermost petals: Outer Side: Red Group 53A. Inner Side: Red Group 53A.
- *After opening, basal petal spots.*—Basal petal spot, outermost petals: Outer Side: White Group N155C. Inner Side: White Group N155B. Basal petal spot, innermost petals: Outer Side: White Group N155C. Inner Side White Group N155C.

General tonality: On open flower Red Group 53A. No change in the general tonality at the end of the 8th day. Afterwards, general tonality is Red Group 53B.

Petals:
- *Petal count.*—Very double.
- *Average range.*—Approximately 55 to 65 petals under normal conditions.
- *Petal reflex.*—Strongly reflexed.
- *Petal edge.*—With point in center of margin.
- *Petal shape.*—Overall shape is obovate. Apex shape is obtuse. Shape of base is obovate.
- *Petal size.*—15-30 mm (l)×15-20 mm (w).
- *Thickness.*—Thick.
- *Petal arrangement.*—Formal.

Petaloids:
- *Petaloid count.*—Average of 3 to 6 per flower.
- *Petaloid size.*—Petaloids are 15 to 30 mm (l)×15 to 20 mm (w).
- *Petaloid color.*—Color of inner side is Red Group 53A. Color of outer side is Red Group 53A with a center stripe of Red Group 49C.
- *Petaloid texture.*—Thick.
- *Margins.*—Undulated.

*Petaloid shape.*—Most commonly oblanceolate, with some petaloids highly irregular. Apex: Round. Base: Attenuate.

Reproductive organs:

*Pistils.*—Approximately 30 present. Stigmas: Location: Slightly inferior in position to anthers. Color: White Group 155C. Styles: Length: About 5 mm long. Color: White Group 155C with intonations of Red Group 46D.

*Stamens.*—Approximately 15 on average and regularly arranged. Anthers: Size: Approximately 3 mm long. Pollen: Absent. Color: Yellow-Orange Group 15C. Filaments: Color: White Group 155D with intonations of Red Group 45D. Length: 4-5 mm.

THE PLANT

Growth: Moderate growth and vigor.

Plant habit: Compact to bushy habit. When grown as a 14 cm pot plant, the average plant height is 25 cm and the average plant width is 18 cm.

Stems:

*Stem color.*—Young wood: Yellow-Green Group 144A. Older wood: Yellow-Green Group 144A.

*Stem surface.*—Young wood: Smooth. Older wood: Smooth.

Prickles: Present.

*Incidence.*—Average of 5 thorns per 10 cm of stem.

*Size.*—Average length of 6 to 7 mm.

*Color.*—Immature prickles: Yellow-Green Group 145 B. Mature prickles: Yellow-Green Group 146C. Senescing to: Grey-Brown Group N199B and N199C.

*Shape.*—Concave.

*Anthocyanin.*—Grey-Red Group 182B at base of thorns on immature foliage.

Leaves and leaflets: Normally 5-7 leaflets on normal leaves in middle of the stem.

*Venation pattern.*—Pyramidal net pattern.

*Leaf size.*—130 mm (l)×80 mm (w).

*Abundance.*—Average.

*Texture.*—Thick texture. Upper side of leaflet: Semi glossy. Under side of leaflet: Matte.

*Color, mature foliage.*—Upper Leaf Surface: Green Group 137A. Lower Leaf Surface: Green Group 137C.

*Color, juvenile foliage.*—Upper Leaf Surface: Green Group 137C. Lower Leaf Surface: Green Group 137C.

*Anthocyanin intonation.*—Present. Intonations of Greyed-Purple Group 187C present on upper and lower surfaces of immature foliage.

Stipules:

*Size.*—15 mm long. 4 mm from distal tip to distal tip.

*Stipule color.*—Yellow-Green Group 144A.

*Margins.*—Very few stipitate glands.

*Shape.*—Apex: Apiculate. Base: Flat.

Petiole:

*Length.*—Average 20 mm.

*Diameter.*—Average 2 mm.

*Petiole color.*—Yellow-Green Group 144A.

*Underneath.*—Smooth.

*Margins.*—With stipitate glands.

Petiole rachis:

*Length.*—Average 26 mm.

*Diameter.*—Average 1.5 mm.

*Color.*—Yellow-Green Group 144A.

*Anthocyanin.*—Present on upper side along margins: Greyed-Purple Group 187C.

*Texture underneath.*—Smooth.

*Margins.*—With very few stipitate glands.

*Prickles.*—Lacking.

Leaflets:

*Size.*—Average size of the terminal leaflet is 50 mm (l)×30 mm (w).

*Shape.*—Ovate. Base: Obtuse. Apex: Acute.

*Margins.*—Finely serrated.

*Surface.*—Upper: Semi-glossy. Lower: Matte.

*Texture.*—Thin.

*Arrangement.*—Odd pinnate.

*Venation.*—Reticulate.

Hips/seed formation: None observed.

Winter hardiness: Unknown.

Disease resistance: Very good resistance to Powdery mildew (*Sphaerotheca pannosa*) and *Botrytis* (*Botrytis cinerea*) diseases under normal growing conditions.

I claim:

1. A new and distinct variety of rose plant, as described and illustrated herein.

* * * * *

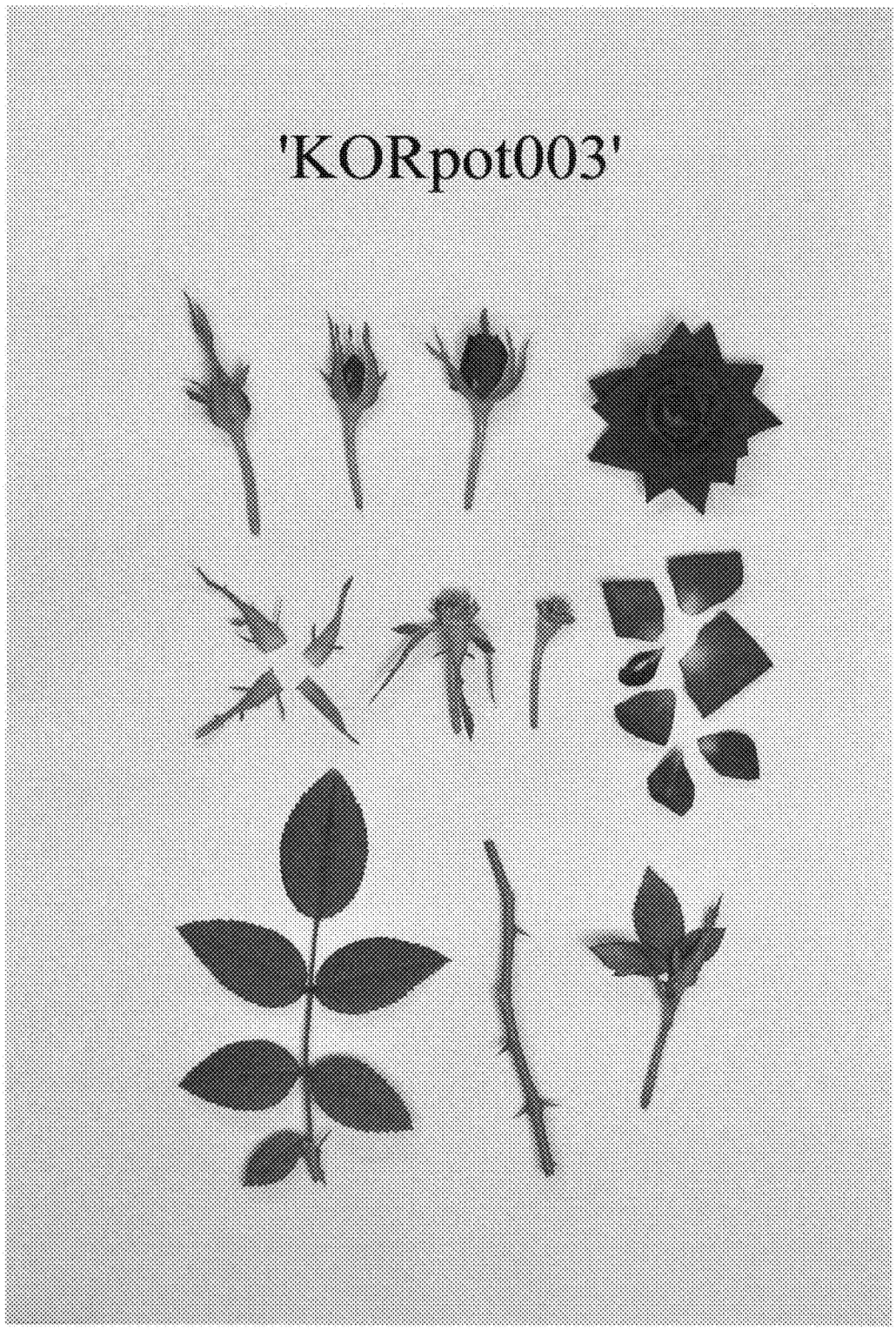
'KORpot003'